US005487306A

United States Patent [19]

Fortes

[11] Patent Number: 5,487,306
[45] Date of Patent: Jan. 30, 1996

[54] PHASE ABERRATION CORRECTION IN PHASED-ARRAY IMAGING SYSTEMS

[75] Inventor: Jose-Mauro P. Fortes, Gavea, Brazil

[73] Assignee: General Electric Company, Schenectady, N.Y.

[21] Appl. No.: 312,363

[22] Filed: Sep. 26, 1994

[51] Int. Cl.⁶ .......................... G01N 29/06; G01N 29/10; G01N 29/24
[52] U.S. Cl. ................................ 73/597; 73/602; 73/626; 128/660.07; 128/661.01
[58] Field of Search ...................... 128/660.06, 660.07, 128/661.01; 73/597, 599, 602, 625, 626, 628

[56] References Cited

U.S. PATENT DOCUMENTS

| | | | |
|---|---|---|---|
| 4,835,689 | 5/1989 | O'Donnell | 73/626 |
| 5,172,343 | 12/1992 | O'Donnell | 73/626 |
| 5,235,983 | 8/1993 | Iida et al. | 128/660.07 |
| 5,268,876 | 12/1993 | Rachlin | 128/661.01 |
| 5,331,964 | 7/1994 | Trahey et al. | 128/661.01 |
| 5,388,461 | 2/1995 | Rigby | 73/597 |

OTHER PUBLICATIONS

Flax et al., "Phase–Aberration Correction Using Signals from Point Reflectors and Diffuse Scatters: Basis Principles", IEEE Trans. on Ultrasonics, Ferroelectrics and Frequency Control, vol. 35, No. 6, Nov. 1988, pp. 758–767.

Primary Examiner—Hezron E. Williams
Assistant Examiner—Rose M. Finley
Attorney, Agent, or Firm—Marvin Snyder

[57] ABSTRACT

An ultrasonic imaging system for performing a scan in which beamforming time delay errors due to nonuniformity in ultrasound propagation speed within the transmission medium are corrected. The system employs a multiple-channel transmitter and receiver. The method estimates and corrects phase aberrations in phased array imaging systems, taking into account additional information associated with array elements which are not necessarily adjacent to each other. The method uses Kalman filtering to obtain an estimate of the phase differences associated with complex samples of pairs of adjacent receive channels. The method incorporates a scheme to detect and correct for the $2\pi$ phase slips that may occur in the data. Because the method provides information on measurement variances, better estimates are obtained by weighting the measurements according to their variances.

15 Claims, 8 Drawing Sheets

PHASE ABERRATION CORRECTION IN PHASED-ARRAY IMAGING SYSTEMS

RELATED APPLICATIONS

This invention is related to J.M.P. Fortes application Ser. No. 08/312,370, still pending, filed concurrently herewith and assigned to the instant assignee.

1. Field of the Invention

This invention relates generally to coherent imaging systems using vibratory energy, such as ultrasound energy, which employ multi-element array transducers. In particular, the invention relates to the reflection method for producing ultrasound images in which a single ultrasonic transducer array is used for both transmission and reception of ultrasonic pulses.

2. Background of the Invention

There are a number of methods in which vibratory energy, such as ultrasound energy, can be used to produce images of objects. In the reflection method, an image is produced in which the brightness of each pixel is a function of the amplitude of the ultrasound reflected from the object to the receiver.

Ultrasonic transducers for medical applications are conventionally constructed from one or more piezoelectric elements sandwiched between a pair of electrodes. When an appropriate voltage pulse is applied, the piezoelectric element emits an ultrasonic pulse into the medium. Conversely, when an ultrasonic pulse strikes the piezoelectric element, the element produces a corresponding voltage across its electrodes. A number of such ultrasonic transducer constructions are disclosed in U.S. Pat. Nos. 4,217,684; 4,425,525; 4,441,503; 4,470,305 and 4,569,231, all of which are assigned to the instant assignee.

When used for ultrasound imaging, the transducer typically has a plurality of piezoelectric elements arranged in an array and driven with separate voltages. In phased-array imaging systems, transmit, steering and focusing are accomplished by making the pulse signals transmitted by individual transducer elements arrive at the same time at a given point in space. By properly controlling the relative time delays of the applied voltages on each element, the ultrasonic waves produced by the piezoelectric elements can be made to combine to produce a net ultrasonic wave focused at a selected point. This focal point can be moved on each successive transmitter firing, so that the transmitted beams can be scanned across the object without moving the transducer.

Similar principles apply when the transducer is employed to receive the reflected sound. The voltages produced at the transducer elements in the array are individually delayed in time and then summed together such that the net signal is dominated by sound reflected from a single receive focal point in the subject. This summed receiver signal is often called the "beamsum".

If the medium is homogeneous and the velocity of sound is known, then the time it takes for a pulse to travel from a given transducer element to a point in space, or vice versa, is determined by simple geometry. Thus, to make all of the pulses arrive in coincidence, time delays are calculated to exactly compensate for geometric path length differences to each element.

For a wave at a single frequency f it is well known that a shift in time $\Delta t$ is equivalent to a shift in phase $\Delta\theta$ through the relationship $\Delta\theta=2\pi\theta\Delta t$. The pulses typically used in ultrasound imaging contain a wide range of frequencies, so this equivalence is only approximate. Some ultrasound imaging systems use the approximate equivalence to combine time delays and phase delays to produce the desired focusing on transmit and/or receive. The process of applying time and/or phase delays to produce focused transmit and receive beams is often called "beamforming."

An ultrasound image is formed by making a series of reflection measurements in a set of desired directions. For each measurement, a focused ultrasonic wave is transmitted. Then the system switches to receive mode and the reflected ultrasonic wave is received, focused and stored. When a complete set of scan directions has been obtained, the ultrasound image is constructed and displayed, and the process then repeats for the next imaging frame. A number of such ultrasonic imaging systems are disclosed in U.S. Pat. Nos. 4,155,258; 4,155,260; 4,154,113; 4,155,259; 4,180,790; 4,470,303; 4,662,223; 4,669,314 and 4,809,184, all of which are assigned to the instant assignee.

Any factor causing a variation in pulse arrival times will produce phase variations across the transducer array, thereby reducing transducer efficiency and its ability to distinguish between on-axis and off-axis signals. For example, spatial inhomogeneities of the refraction index can lead to significant variations in propagation velocity, inducing phase delays (phase aberrations) that reduce the efficiency and the directivity of the transducer. If the sound speed is not constant, sound pulses transmitted from certain elements in the array can arrive earlier or later than expected at the desired focal point and will not properly combine with the other pulses. As a result, the net transmitted wave will not be optimally focused. Similarly, on reception, the signals on each element in the array will not be delayed optimally before summing so that the receive focusing will be degraded. If the deviations from the assumed propagation times could be measured or estimated, the ultrasound image could be improved by correcting the applied time delays for the deviations.

The human body is known to consist of many different tissues with differing sound speeds. Despite this, in medical applications the assumption of constant sound speed produces good images on many patients. However, the distribution of the various tissue types varies widely with patients, and some patients are only poorly imaged. The body wall, in particular, which includes relatively thick muscle and fat layers with sound speeds significantly different from the average sound speeds of the internal organs, can degrade the image for some patients. The solution to this problem involves correcting for phase aberrations so that transducer efficiency and directivity are restored. There would be a substantial medical benefit if the images of these patients could be improved by correcting for nonuniformity in the ultrasound propagation speed in their bodies. Such phase aberration corrections may need calculation for each separate transmit/receive direction, since the ultrasound propagation speed nonuniformities may vary significantly with beam direction. The corrections may also require calculation on a real-time basis due to patient and transducer motion in clinical applications.

A general phase aberration correction method applicable to coherent imaging systems using a sampled aperture has been proposed by Flax and O'Donnell, *Phase-Aberration Correction Using Signals from Point Reflectors and Diffuse Scatterers: Basic Principles*, IEEE Trans. on Ultrasonics, Ferroelectrics and Frequency Control, Vol. 35, No. 6, November 1988. Signals emanating from a point source, or a small region of distributed scatterers, exhibit uniformity across the transducer array. Since focus exists only if the signal from a point radiator arrives at each transducer element in coincidence, the degree to which coincidence is violated is a measure of the "lack of focus" or "arrival time (phase) error." If the signal at each element is very similar, then the time offsets can be readily detected and quantified using a cross-correlation measurement between any two elements. In particular, the time offset of the peak in the cross-correlation function is a direct measure of the arrival time difference between neighboring channels. The method of Flax and O'Donnell uses only phase difference information associated with adjacent elements in a phased-array system. However, phase difference estimates based only on measurements taken from adjacent array elements can have reasonably large variances. Consequently, such estimates have low reliability. The reliability of these estimates can be considerably improved if additional information on phase differences between signals in nonadjacent array elements is used.

SUMMARY OF THE INVENTION

An object of the invention is to provide a method and apparatus for correcting for focusing degradation in an ultrasound imaging system caused by variations in ultrasound propagation speed within the transmission medium.

Briefly, in accordance with a preferred embodiment of the invention, a method and apparatus are provided to estimate and correct phase aberrations in phased array imaging systems by taking into account additional information associated with array elements which are not necessarily adjacent to each other. A recursive algorithm based on the Kalman filter is employed, along with a scheme to detect and handle $2\pi$ phase slips that may occur in the data. By using information on measurement variances, better estimates are produced by weighting the measurements according to their variance.

In particular, the apparatus of the invention includes a multi-element ultrasonic transducer; a transmitter which applies to the separate transducer elements pulses delayed by amounts necessary to steer an ultrasonic beam in a desired direction; a receiver responsive to each transducer element for providing a separate delay to the echo signal produced by each transducer element to form a receive beam steered in the desired direction; and a phase aberration correction circuit responsive to the receiver and operable to measure the phase aberration error for each transducer element using a recursive and Kalman filter-based algorithm. The phase aberration correction means produces a correction phase rotation for each transducer element, using acquired beam data. The set of correction phase rotations thus produced is applied on subsequent transmitter firings for the same beam direction to correct the timing of the pulses applied to the respective transducer elements by the transmitter. The set of correction phase rotations is also employed to correct the delays imposed by the receiver on the echo signals produced by the respective transducer elements.

Because the algorithm employed in the present invention is recursive, the algorithm is able to use, at a given step, extant (i.e., current) estimates of the phase differences as a reference for detecting and handling $2\pi$ slips in measurements being processed at that step. These current estimates are indeed more reliable than the initial one since, unlike the initial one, they are based on past data.

When the phase-disturbing medium is close to the detecting array, as for example in medical imaging, diffraction can cause some of the array elements to receive very low-energy signals. If the reference signal has low-energy entries, it becomes very difficult to detect the $2\pi$ phase slips. In this case it is necessary to use as a reference a better estimate of the phase differences, which would reduce the chance of having low-energy entries.

To be able to use information on measurement noise variances, it is necessary to determine how these variances relate to the magnitude of the correlation coefficients of the signals involved. In arriving at the present invention, an analytical expression relating the measurement variances to the magnitude of the correlation coefficients was derived. This expression is adequate whenever multiple scatterers are present and satisfies the conditions for the central limit theorem to hold.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing(s) in which:

DETAILED DESCRIPTION OF THE PREFERRED EMBODIMENTS

Figure 1:
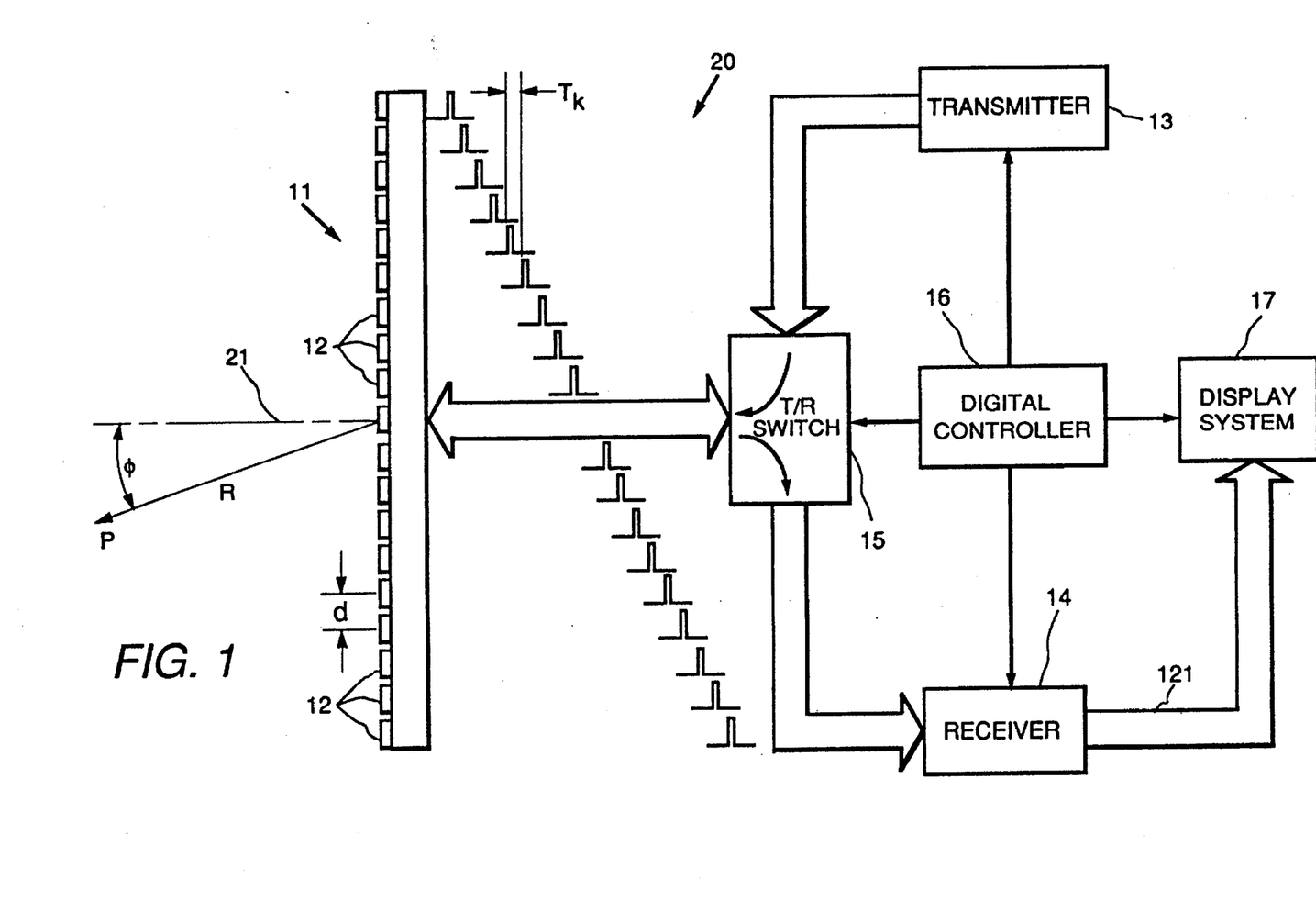
FIG. 1 is a block diagram of an ultrasonic imaging system employing the present invention.

As shown in FIG. 1, a vibratory energy imaging system includes a transducer array 11 comprised of a plurality of separately driven elements 12 which each produce a burst of vibratory energy, such as ultrasonic energy, when energized by a pulse produced by a transmitter 13. The vibratory energy reflected back to transducer array 11 from the subject under study is converted to an electrical signal by each transducer element 12 and applied separately to a receiver 14 through a set of transmit/receive (T/R) switches 15.

Transmitter 13, receiver 14 and switches 15 are operated under control of a digital controller 16 responsive to commands by a human operator. Each scan line in the image is constructed by acquiring a series of echoes. Switches 15 are set to their transmit positions, transmitter 13 is gated on momentarily to energize each transducer element 12, switches 15 are then set to their receive positions, and the subsequent echo signals produced by each transducer element 12 are applied to receiver 14. The separate echo signals from each transducer element 12 are combined in receiver 14 to produce a single echo signal corresponding to a single scan line. A display system 17 receives the series of data samples produced by receiver 14 for all the scan lines and converts the data to a form producing one frame of the desired image.

Transmitter 13 drives transducer array 11 such that the vibratory energy produced (e.g., ultrasonic energy) is directed, or steered, and focused in a beam. A complete scan can therefore be performed by moving this beam through a set of angles $\phi_i$. To accomplish this, transmitter 13 imparts a time delay $T_{t,k}$ $k=1,\ldots,N$, to the respective pulses 20 that are applied to N transducer elements 12. Time delays $T_{t,k}$ are chosen so that the pulses from each transducer element will arrive at the desired transmit focus point $(R, \phi_i)$ simultaneously.

Figure 2:
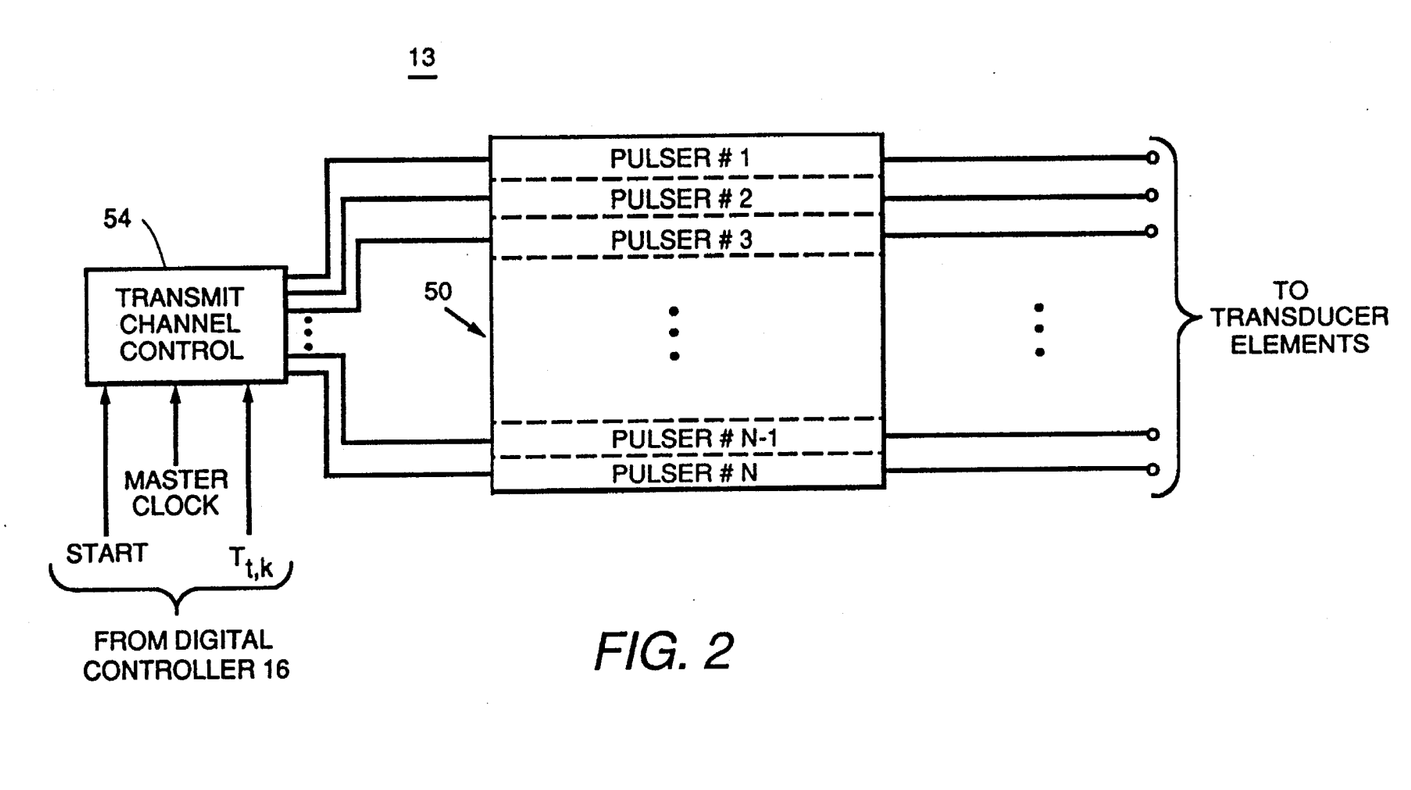
FIGS. 2 and 3 are block diagrams of a transmitter and a receiver, respectively, which form part of the system of FIG. 1.

As shown in FIG. 2, transmitter 13 comprises a transmit channel control section 54 and pulsers 50. The transmit channel control receives from digital controller 16, shown in FIG. 1, two control signals, START and MASTER CLOCK, and the transmit time delays $T_{t,k}$. Using the MASTER CLOCK signal as the timing reference, the transmit channel control generates a timing signal for each of pulsers 50 at the respective times $T_{t,k}$ after reception of the START signal, which signals the beginning of a single transmit/receive beam cycle. Upon reception of its respective timing signal, each pulser generates an electrical pulse which is conveyed to the corresponding transducer element through a respective one of T/R switches 15, shown in FIG. 1. The transducer element converts the electrical pulse into an ultrasonic pulse.

The echo signals produced by each burst of ultrasonic energy emanate from reflecting objects located at successive positions along the scan line direction. These are sensed separately by each element 12 of transducer array 11 shown in FIG. 1. Receiver 14, shown in FIG. 1, amplifies these separate echo signals, imparts the proper time delay to each, and sums them together to provide a single echo signal which accurately indicates the total ultrasonic energy reflected from the receive focal point P, shown in FIG. 1. The time delays for the receiver are calculated as for the transmitter by taking into account the propagation time from the focal point to each transducer element.

Figure 3:
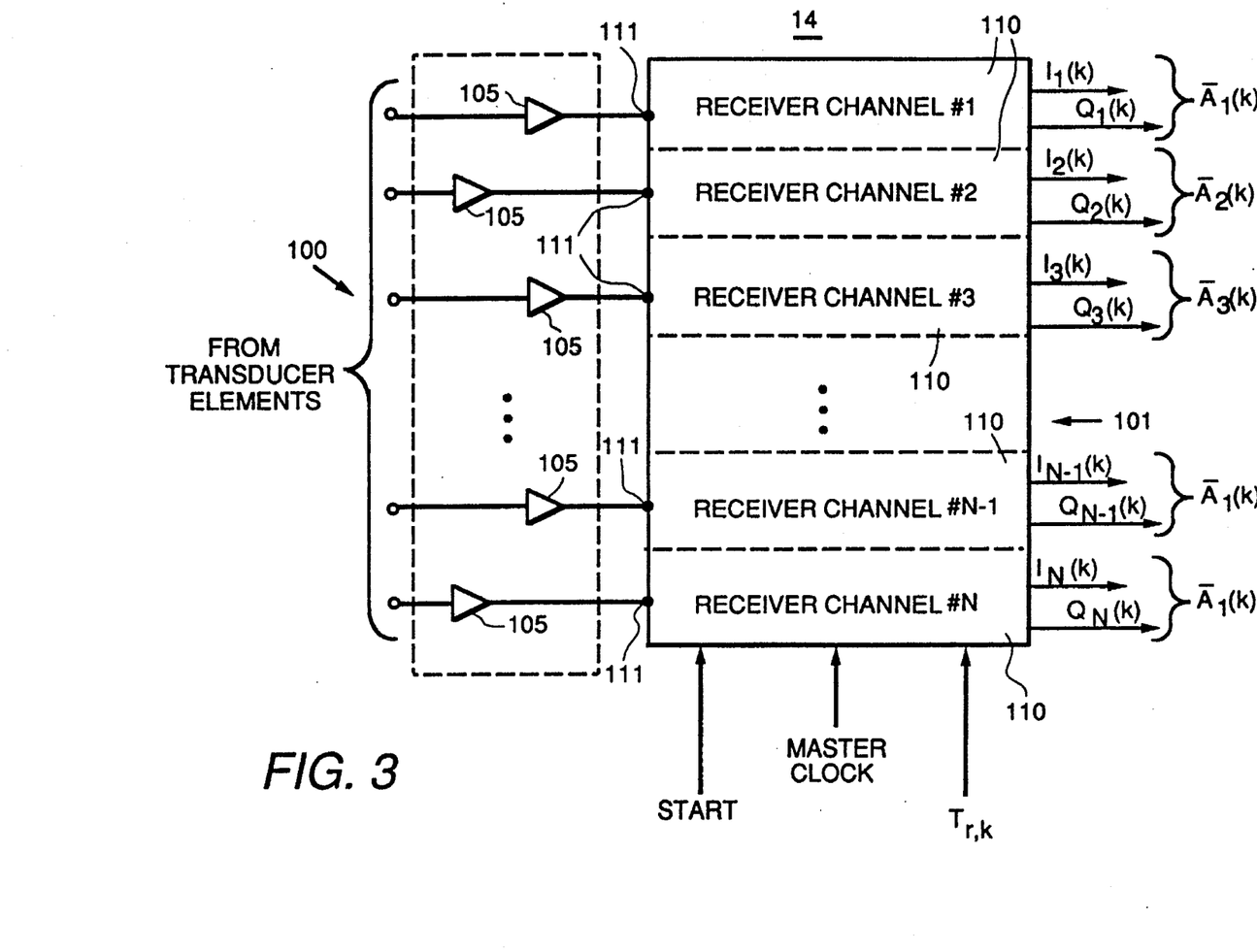

As shown in FIG. 3, receiver 14 comprises an amplifier section 100 and a receive beamforming section 101. Each transducer element 12, shown in FIG. 1, is connected through a respective one of T/R switches 15, shown in FIG. 1, to an amplifier 105 which amplifies the echo signal received by the transducer element. The amplified signal from each amplifier is applied to a respective receiver channel 110. Each receiver channel receives from digital controller 16, shown in FIG. 1, two control signals, START and MASTER CLOCK, and the corresponding receive time delay $T_{r,k}$. Each receiver channel samples and demodulates the analog echo signal from the amplifier, producing a stream of digital complex signal samples $\overline{A}(k)$ having components $I(k)$ and $Q(k)$. The I and Q signals are digital numbers representing the in-phase and quadrature components of the demodulated echo signal. Using the MASTER CLOCK signal, these samples are delayed by the receiver channels by the corresponding time delays $T_{r,k}$ with respect to the START signal, which signals the beginning of a single transmit/receive beam cycle.

The present invention estimates phase aberration due to spatial inhomogeneities in the ultrasound-propagating medium and produces the phase rotations $\hat{\theta}_i$, which are then applied to the complex signal samples to correct the phase aberrations. Corrections can be applied in either the transmission or reception mode.

Figure 4:
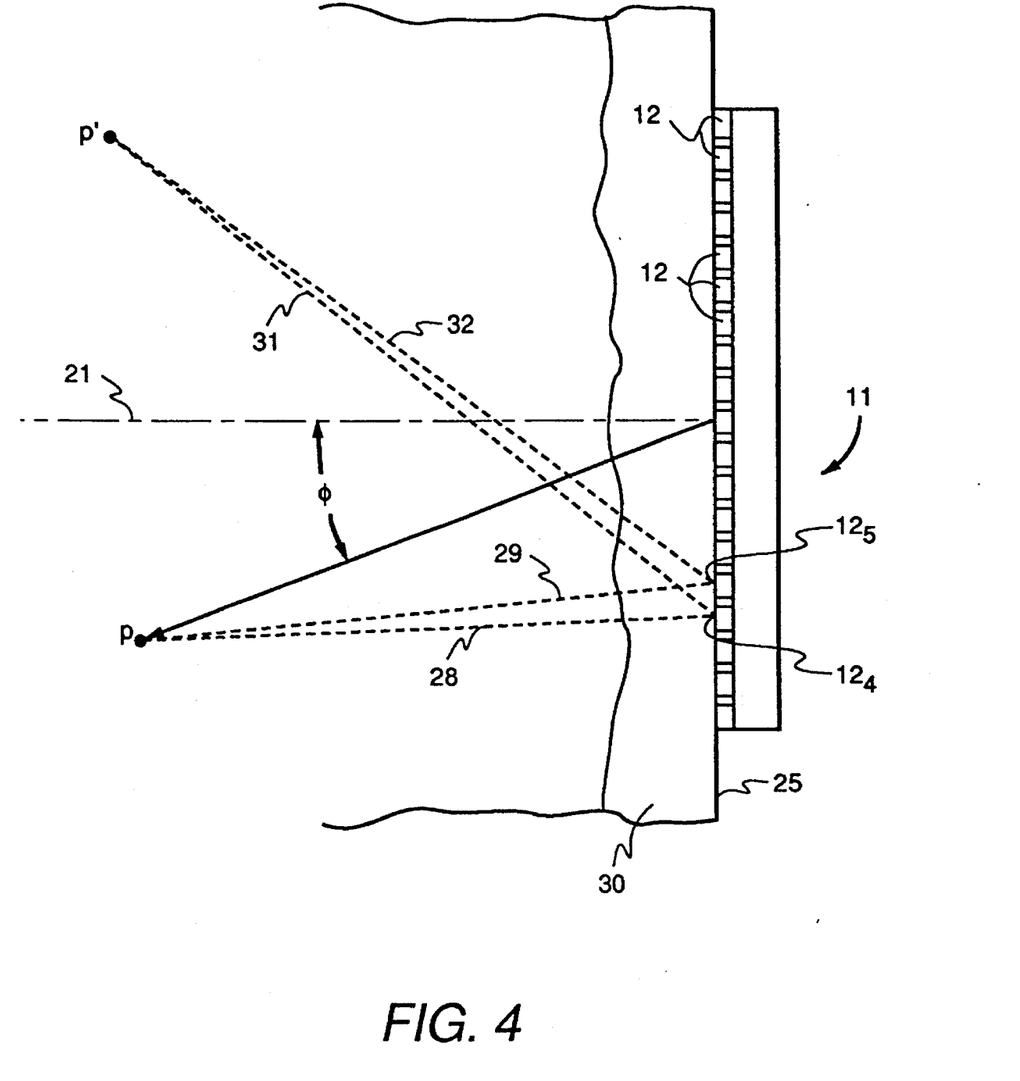
FIG. 4 is a schematic representation of the effect of nonuniformities in the sound transmission medium.

In clinical applications the assumption of uniform ultrasound propagation speed along the beam path can often be invalid. As shown in FIG. 4, ultrasonic transducer 11 is typically placed on the patient's skin 25. Ultrasonic energy transmitted into and received from the region of interest may pass through several layers of tissue which are likely to have different ultrasound propagation properties, in particular, different ultrasound transmission speeds. The presence of tissue layers with ultrasound transmission speeds other than that assumed for the transmit and receive time delay equations causes phase aberrations. When the layers have irregular boundaries, the phase aberration angle can vary from element to element, resulting in substantial degradation of the transmit and receive focusing. Consider as an example the case shown in FIG. 4 in which a boundary 26 between two tissue layers is irregularly shaped. When beam samples are acquired from point P at steering angle $\phi$, ultrasound energy conveyed between point P and two separate array elements 12$_4$ and 12$_5$ is propagated quite differently due to the irregularity of boundary 26. This is illustrated by the respective dashed lines 28 and 29 which reveal that the ultrasound path length in tissue layer 30 is longer for transducer element 12$_5$ than for transducer element 12$_4$. This difference in path length within tissue layer 30 extending to the two transducer elements 12$_4$ and 12$_5$ causes different phase aberration angles for these two elements. The same tissue layer may cause an element-dependent phase aberration for other transducer elements 12, and the same tissue layer may cause an element-dependent phase aberration for the same elements 12$_4$ and 12$_5$ at different steering angles $\phi$. This is illustrated by the ultrasound paths 31 and 32 to a point P' which have very similar path lengths within tissue layer 30. Thus, in general, phase aberrations caused by nonuniformities in the sound-propagating medium are different for each transducer element 12 and for each beam direction $\phi_i$ acquired during the scan.

Consider a phased array containing n+1 transducer elements and let $\theta_{i,j}$ denote the phase difference between the signals reaching array elements i and j. Let x denote the vector whose entries are the phase differences between signals received by adjacent elements, that is, $$x = \begin{pmatrix} \theta_{1,2} \\ \theta_{2,3} \\ \cdot \\ \cdot \\ \cdot \\ \theta_{n,n+1} \end{pmatrix} \quad (1)$$

Also, let $y_k$ denote a noisy measurement of the phase difference between signals reaching any pair of array elements, for example, elements i and j, that is, $$y_k = \theta_{i,j} + w_k \quad (2)$$

where $w_k$ denotes a measurement noise with variance $\lambda_k$. Note that Eq. (2) can be written as $$y_k = C_k x + w_k \quad (3)$$

where $C_k$ is the 1×n vector with entries $C_{kl}$, $l=1,\ldots,n$, given by $$C_{kl} = \begin{cases} 1 & \text{if } i \leq l \leq j-1 \\ 0 & \text{otherwise} \end{cases} \quad (4)$$

The vector x, assumed to be time invariant ($x_{k+1}=x_k$), can be estimated from a set of noisy measurements $y_k$, $k=1,\ldots,M$, associated with M different pairs of array elements. This is done through a Kalman filter algorithm, which establishes that, in this particular case, the estimate $\hat{k}_k$ of x, given all past measurements $y_1, y_2, \ldots, y_k$, is given by $$\hat{x}_k \hat{x}_{k-1} + K_k(y_k - C_k \hat{x}_{k-1}) \quad (5)$$

with $$K_k = P_{k-1} C_k^T (C_k P_{k-1} C_k^T + \lambda_k)^{-1} \quad (6)$$

$$P_k = P_{k-1} - K_k C_k P_{k-1} \quad (7)$$

where $\lambda_k$ represents measured phase difference variances.

In Eq. (6), $K_k$ and $P_k$ are, respectively, the Kalman gain and the error covariance matrix at step k.

The Kalman filter allows the measurements to be processed one by one, as in Eq. (5), or grouped in m-dimensional vectors and used in block. In the latter case, at each step, a m×m square matrix has to be inverted and the m×m covariance matrix $\Lambda_k$ of the measurement noise vector $w_k$ has to be known. To compensate for this additional work, the error covariance matrix $P_k$ has to be updated less frequently (i.e., at a rate m times smaller than that used when measurements are processed one by one).

Figure 5:
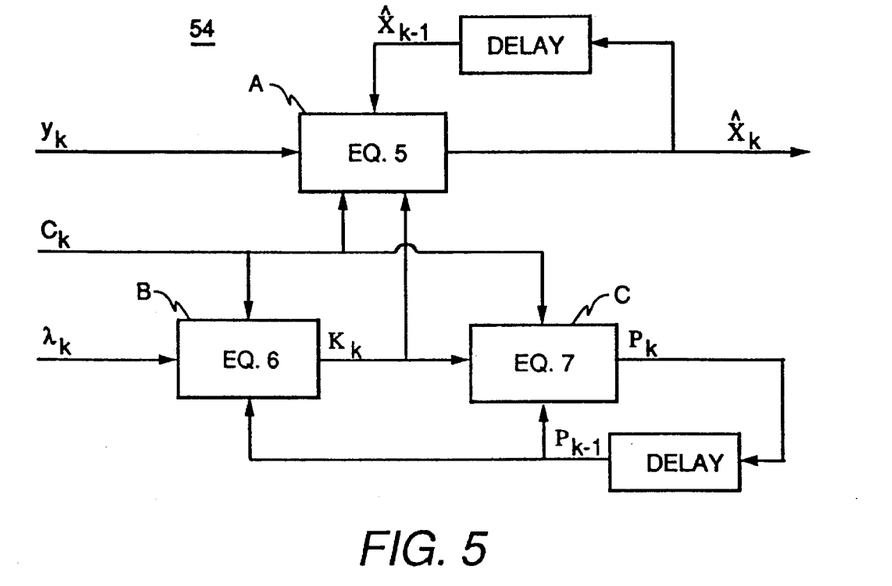
FIG. 5 is a block diagram of a Kalman filter utilized in the present invention.
Figure 6:
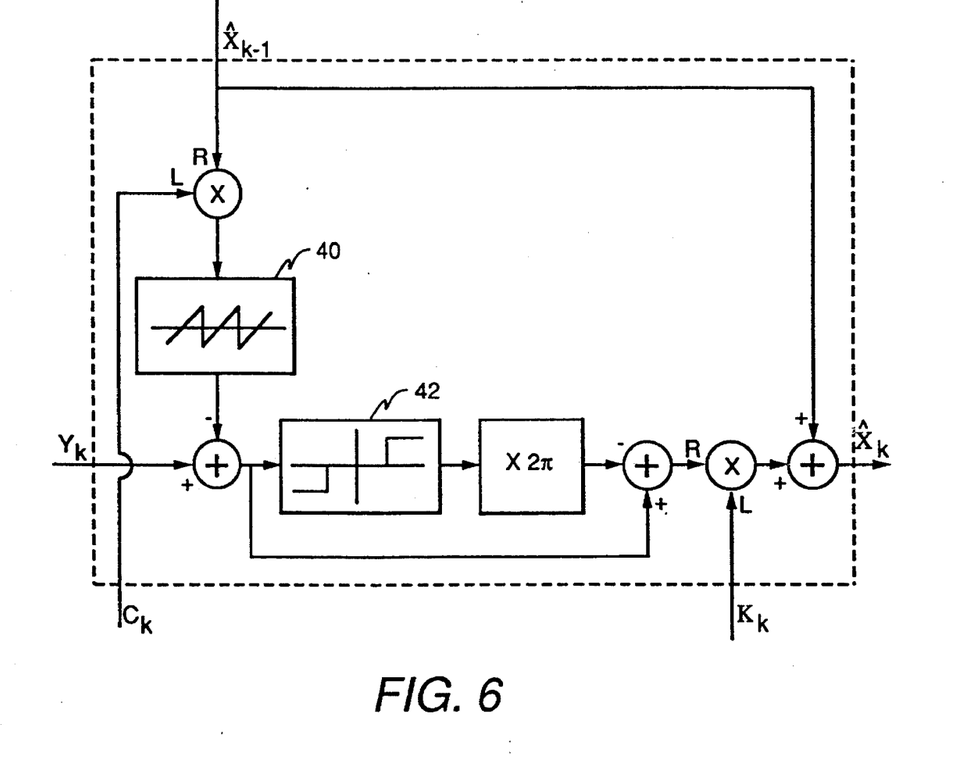
FIGS. 6 through 8 are block diagrams of the steps implemented by Blocks A through C shown in FIG. 5.
Figure 7:
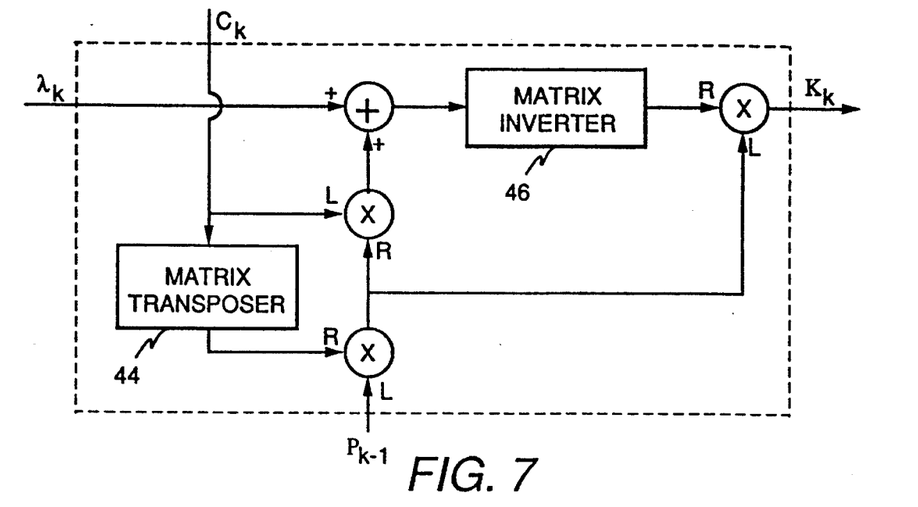
Figure 8:
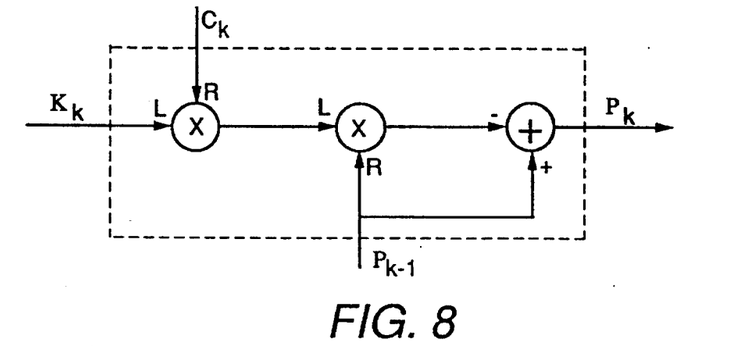

A block diagram of the Kalman filter 54 is presented in FIG. 5. Blocks A, B and C implement, respectively, Eqs. (5), (6) and (7). Block diagrams of the steps implemented by blocks A, B and C are presented in FIGS. 6, 7 and 8, respectively. The diagram of FIG. 6 incorporates a scheme to detect and take into consideration measurement of $2\pi$ phase slips in the received signal based on the previous estimate of vector x. This scheme basically compares a modulo $2\pi$ version of the previous estimate $\hat{x}_{k-1}$ with the measurement $y_k$ and uses their difference to detect and correct for the $2\pi$ phase slips. A modulo $2\pi$ function is performed at block 40 to introduce $2\pi$ phase slips into $\hat{x}_{k-1}$ to ensure that $C_k \hat{x}_{k-1}$ is between $-\pi$ and $+\pi$, as is $y_k$. A quantizer 42 determines the number of $2\pi$ phase cycles to be used in the correction of phase slips. In the implementation of FIG. 7, $C_k$ is transposed at block 44 and $(C_k P_{k-1} C_k^T + \lambda_k)$ is inverted at block 46. The other arithmetic operators in FIGS. 6, 7 and 8 are as indicated by the arithmetical symbols indicated therein.

Figure 9:
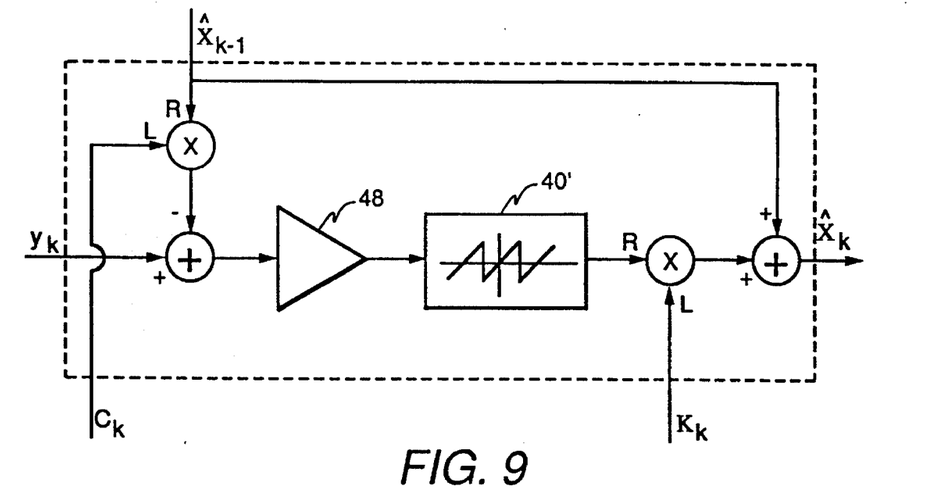
FIG. 9 is a block diagram showing an alternative implementation of Block A shown in FIG. 5.

An alternative implementation for block A (e.g., Eq. (5)) is presented in FIG. 9. The signal $(y_k - C_k \hat{x}_{k-1})$ is amplified by an amplifier 48 and then converted into a value between $-\pi$ and $+\pi$ by a modulo $2\pi$ function 40'. Although the schemes of FIGS. 6 and 9 are not exactly equivalent, their performance, in terms of correcting for $2\pi$ phase slips, is essentially the same.

Since the noisy phase differences $y_k$ are not directly measured, they have to be estimated from available data and inserted into the Kalman filter algorithm as follows. Let $\bar{A}_i(k)$ and $\bar{A}_j(k)$, $k=1,\ldots,K$, be complex samples (e.g., $\bar{A}_i(k) = I_i(k) + jQ_i(k)$) of the signals reaching array elements i and j and let $\mu$ denote their correlation coefficient. Assume that $\mu$ is known and equal to $\bar{\mu}_{ij}$, that is, $$\bar{\mu} = \bar{\mu}_{ij} = \rho_{ij} e^{j\psi_{ij}} \quad (8)$$

The observables $y_k$ for the Kalman algorithm can be taken as the minimum mean square error estimate of the modulo $2\pi$ phase difference $(\theta_i - \theta_j)_{Mod\ 2\pi}$, given $\bar{\mu} = \bar{\mu}_{ij}$, which is shown to be equal to $\psi_{ij}$. The variance of these observables depend only on $\rho_{ij}$ and is given by $$\sigma^2_{\delta ij}(\rho_{ij}) = \frac{(1-\rho_{ij}^2)}{\pi} \int_0^\pi \frac{\eta^2 \cos\eta \left[ \rho_{ij}\sin^{-1}(\rho_{ij}\cos\eta) + \frac{\pi \rho_{ij}}{2} + \sqrt{\sec^2\eta - \rho_{ij}^2} \right]}{2\pi^2(1-\rho_{ij}^2\cos^2\eta)^{3/2}} d\eta \quad (9)$$

These facts suggest that $y_k$ and $\lambda_k$ should be taken, respectively, as $$y_k = \psi_{ij} \quad (10)$$

and $$\lambda_k = \sigma^2_{\delta ij}(\rho_{ij}) \quad (11)$$

Figure 10:
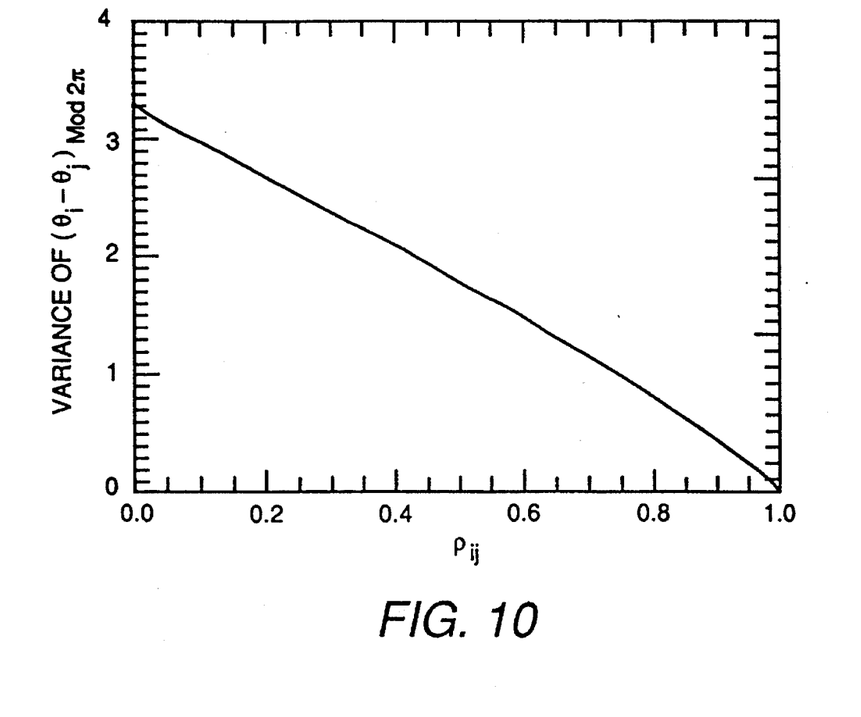
FIG. 10 is a plot of the variance of the modulo $2\pi$ phase difference between complex samples reaching array elements i and j as a function of the magnitude $\rho ij$ of the correlation coefficient of the samples.

The integration indicated in Eq. (9) can be performed numerically. The resulting curve is shown in FIG. 10.

When the value $\bar{\mu}_{ij}$ of the correlation coefficient is not known, it must be estimated from the available data $\bar{A}_i(k)$ and $\bar{A}_j(k)$, $k=1,\ldots,K$. The estimated value of the correlation coefficient is then obtained by $$\bar{\mu}_{ij} = \hat{\rho}_{ij} e^{j\hat{\omega}_{ij}} = \frac{J_{ij}}{\sqrt{J_{ii} J_{jj}}} \quad (12)$$

with $$J_{ij} = \sum_{k=1}^{K} \bar{A}_i(k) \bar{A}_j^*(k) \quad (13)$$

Figure 11:
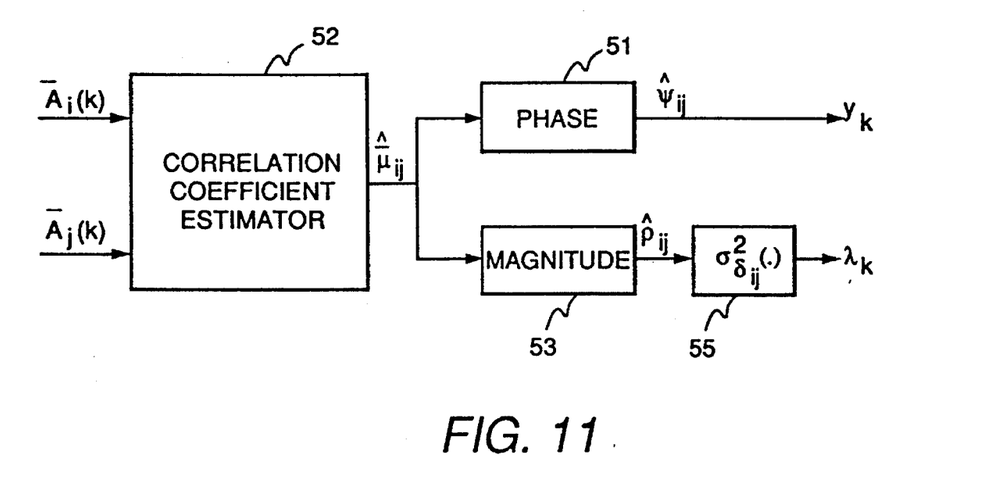
FIG. 11 is a block diagram of a cross-correlation arrangement for generating phase differences $y_k$ and phase difference variances $\lambda_k$ from digital signal samples $\overline{A}_i(k)$ and $\overline{A}_j(k)$ in accordance with the invention.

A block diagram of the scheme for generating $y_k$ and $\lambda_k$ from $\bar{A}_i(k)$ and $\bar{A}_j(k)$ is presented in FIG. 11. The estimated correlation coefficients $\hat{\mu}$ are calculated using a conventional correlation coefficient estimator 52. The correlation coefficients are then separated into their phase and magnitude components by a phase detector 51 and a magnitude detector 53, respectively. A nonlinear function generator 55 responsive to magnitude detector 53 produces the estimate $\lambda_k$ representing the variance of the phase of the correlation coefficient $\bar{\mu}$.

Figure 12:
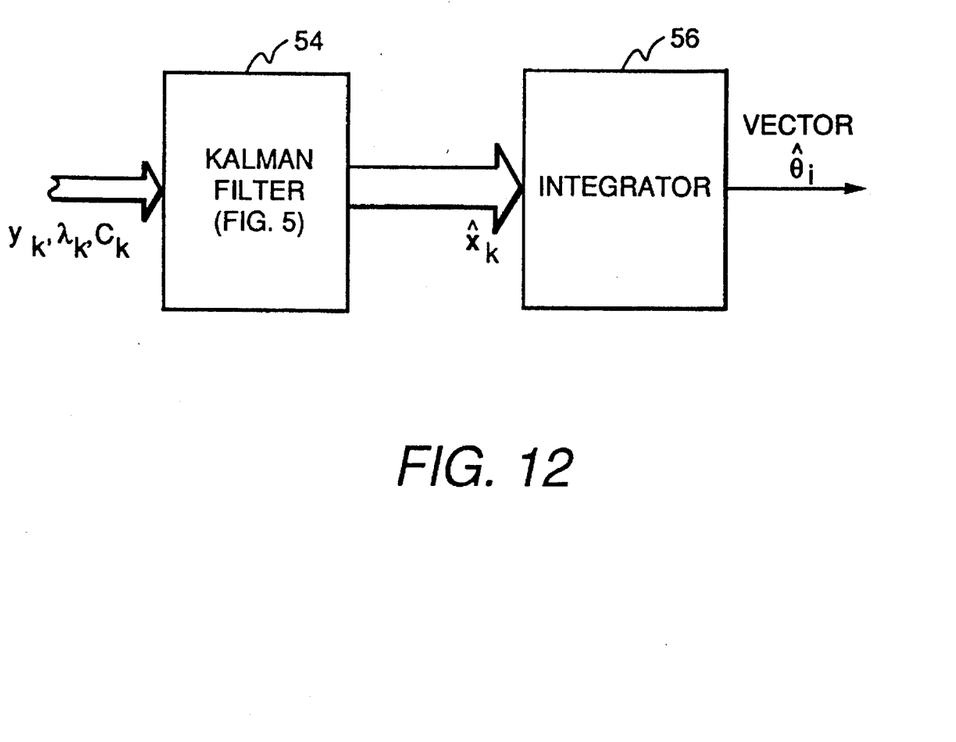
FIG. 12 is a block diagram of a scheme for generating a phase aberration profile $\hat{\theta}$ from noisy measurements $y_k$ in accordance with the invention.

Implementation of the algorithm is performed by determining $y_k$ and $\lambda_k$ in accordance with FIG. 11 and then supplying these values to the Kalman filter of FIG. 5 to generate estimates of the phase differences x induced by the phase-aberrating medium. As shown in the block diagram of FIG. 12, the phase difference estimates produced by Kalman filter 54 are integrated by an integrator 56 to generate an estimate $\hat{\theta}$ of the phase aberration profile, where $$\hat{\theta} = \begin{pmatrix} \hat{\theta}_1 \\ \hat{\theta}_2 \\ \cdot \\ \cdot \\ \cdot \\ \hat{\theta}_n \end{pmatrix}$$

Figure 13:
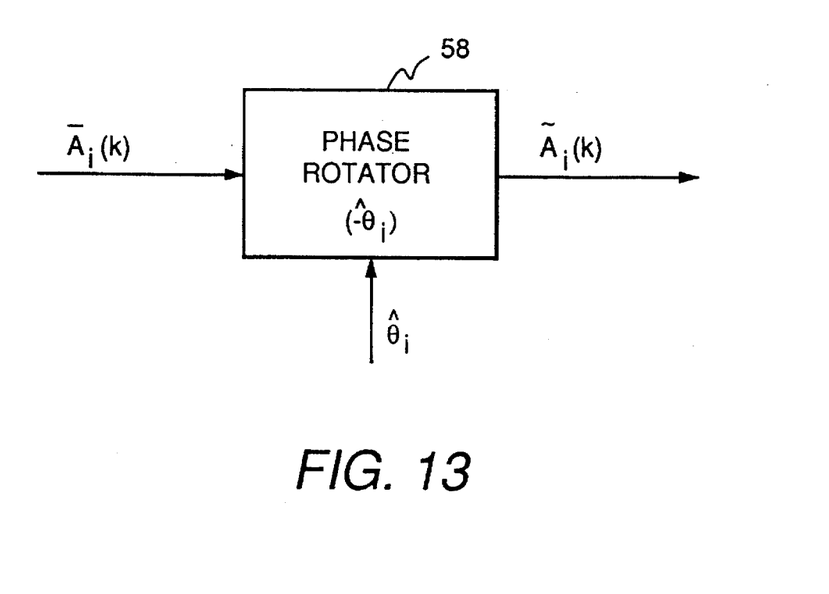
FIG. 13 is a block diagram showing correction of phase aberration by phase rotation of complex samples in accordance with the invention.

The estimates $\hat{\theta}_i$ in the phase aberration profile can then be used to correct phase aberrations by use of a phase rotator 58, as shown in FIG. 13, to rotate the phase of the complex samples such as $\overline{A}_i(k)$, thereby improving image quality.

One of the most time-consuming tasks in the phase aberration correction scheme is the computation of magnitudes of the correlation coefficients from the available measurements (see Eqs. (12) and (13) and FIG. 7). A much faster alternative is to use a scheme that would not compute these magnitudes from the measurements. This alternative becomes a possibility by making use of the Van Cittert-Zernike theorem. According to this theorem, the magnitude of the spatial correlation function for a one-dimensional aperture such as a linear array is a triangle function whose base is twice the array size. In this case, $$\rho_{ij} = \frac{n+1-|i-j|}{n+1} \quad (14)$$

where n+1 denotes the total number of array elements. In this case the magnitude of the correlation coefficient is a function of the distance, measured in number of array elements, between the two elements being considered.

The use of Eq. (14) brings additional advantages to the implementation of the Kalman algorithm. From FIG. 5 it can be seen that if the variances $\lambda_k$ do not depend on the measurements, the Kalman gains $K_k$ can be precomputed and stored. This reduces the implementation of the Kalman algorithm to the implementation of Block A, to which the $C_k$'s and the precalculated $K_k$'s will be supplied. The loss resulting from the use of this alternative is not substantial.

The foregoing preferred embodiments have been disclosed for the purpose of illustration. Although primarily developed for ultrasound medical imaging systems, the present invention is applicable to other types of sampled aperture imaging systems, such as phased array and synthetic aperture radar or sonar systems. Many variations and modifications which do not depart from the broad concept disclosed herein will be readily apparent to those skilled in the art. It is therefore to be understood that all such variations and modifications as fall within the true spirit of the invention are intended to be encompassed by the appended claims.

What is claimed is:

1. A sampled aperture imaging system comprising:
   a plurality of transducers arranged in a sequence to form an array;
   means for selectively operating said transducers in a transmission mode to produce propagating energy pulses from electrical driving signals;
   means for selectively operating said transducers in a reception mode to produce analog electrical detection signals in respective ones of a plurality of receive channels in response to detection of reflected energy pulses, each receive channel being coupled to a corresponding one of said transducers;
   means for sampling and demodulating said analog electrical detection signals into digital complex signal samples; and
   Kalman filter means for recursively estimating phase differences associated with digital complex signal samples in pairs of adjacent receive channels.

2. The sampled aperture imaging system as defined in claim 1, further comprising cross-correlation means for generating noisy measurements of phase differences associated with digital complex signal samples of pairs of adjacent and non-adjacent receive channels and their variances, the output signal of said cross correlation means supplied input to said Kalman filter means.

3. The sampled aperture imaging system as defined in claim 2, wherein said cross-correlation means comprises a correlation coefficient estimator, a phase detector responsive to said correlation coefficient estimator, a magnitude detector responsive to said correlation coefficient estimator, and a nonlinear function generator responsive to said magnitude detector.

4. The sampled aperture imaging system as defined in claim 1, further comprising integrating means coupled to receive said estimated phase differences from said Kalman filter means for estimating a phase aberration profile comprising a plurality of correction phase aberration angles.

5. The sampled aperture imaging system as define in claim 4, further comprising phase rotating means for correcting the phase of each of said complex signal samples by an amount equal to a respective one of said correction phase aberration angles.

6. The sampled aperture imaging system as defined in claim 1, wherein said Kalman filter means includes a quantizer for determining how many $2\pi$ phase cycles are required to correct for $2\pi$ phase slips in signals received by said transducers.

7. A sampled aperture imaging system comprising a plurality of receive channels and a plurality of transducers, each one of said channels being coupled to a respective one of said transducers, said system being adapted to form complex signal samples in response to detection by said transducers of reflected energy pulses, and a Kalman filter for recursively estimating phase differences associated with complex signal samples in pairs of adjacent receive channels.

8. The sampled aperture imaging system as defined in claim 7, further comprising cross-correlation means for generating noisy measurements of the phase differences associated with complex samples of pairs of adjacent and nonadjacent receive channels and their variances, the output signal of said cross correlation means being supplied to said Kalman filter.

9. The sampled aperture imaging system as defined in claim 8, wherein said cross-correlation means comprises a correlation coefficient estimator, a phase detector responsive to said correlation coefficient estimator, a magnitude detector responsive to said correlation coefficient estimator, and a nonlinear function generator responsive to said magnitude detector.

10. The sampled aperture imaging system as defined in claim 7, further comprising integrating means coupled to receive said estimated phase differences from said Kalman filter means for estimating a phase aberration profile comprising a plurality of correction phase aberration angles.

11. The sampled aperture imaging system as defined in claim 10, further comprising phase rotating means for correcting the phase of each of said complex signal samples by an amount equal to a respective one of said correction phase aberration angles.

12. The sampled aperture imaging system as defined in claim 7, wherein said Kalman filter includes a quantizer for determining how many 2π phase cycles are required to correct for 2π phase slips in signals received by said transducers.

13. A method for estimating phase aberrations induced in a sampled aperture imaging system by a phase-aberrating medium, comprising the steps of:

generating noisy measurements of the phase differences associated with complex samples of pairs of adjacent and nonadjacent receive channels;

recursively estimating the phase differences associated with complex samples in pairs of adjacent receive channels; and integrazing the recursively estimated phase differences to obtain an estimate of the phase aberration profile.

14. The method as defined in claim 13, wherein the step of generating noisy measurements of the phase differences comprises the step of cross-correlating the complex samples of said pairs of adjacent and nonadjacent receive channels.

15. The method as defined in claim 13, wherein the step of recursively estimating the phase differences comprises the step of Kalman filtering.

* * * * *